United States Patent
Stahl et al.

(10) Patent No.: US 10,420,784 B2
(45) Date of Patent: Sep. 24, 2019

(54) MIXTURE OF NON-DIGESTIBLE OLIGOSACCHARIDES FOR STIMULATING THE IMMUNE SYSTEM

(71) Applicant: N.V. Nutricia, Zoetermeer (NL)

(72) Inventors: Bernd Stahl, Utrecht (NL); Alma Jildou Nauta, Utrecht (NL); Johan Garssen, Utrecht (NL); Eric Samain, Gieres (FR); Sophie Drouillard, Claix (FR)

(73) Assignee: N.V. NUTRICIA, Zoetermeer (NL)

( * ) Notice: Subject to any disclaimer, the term of this patent is extended or adjusted under 35 U.S.C. 154(b) by 0 days.

(21) Appl. No.: 15/360,524

(22) Filed: Nov. 23, 2016

(65) Prior Publication Data

US 2017/0232022 A1 Aug. 17, 2017

Related U.S. Application Data

(63) Continuation of application No. 13/383,823, filed as application No. PCT/NL2010/050446 on Jul. 12, 2010, now abandoned.

(60) Provisional application No. 61/255,950, filed on Oct. 29, 2009.

(30) Foreign Application Priority Data

Jul. 15, 2009 (EP) .................................... 09165543

(51) Int. Cl.
| | |
|---|---|
| *A61K 31/702* | (2006.01) |
| *A61K 39/145* | (2006.01) |
| *A61K 39/12* | (2006.01) |
| *A23L 33/00* | (2016.01) |
| *A23L 33/10* | (2016.01) |
| *A61K 39/39* | (2006.01) |
| *A61K 39/00* | (2006.01) |

(52) U.S. Cl.
CPC ............ *A61K 31/702* (2013.01); *A23L 33/10* (2016.08); *A23L 33/40* (2016.08); *A61K 39/12* (2013.01); *A61K 39/145* (2013.01); *A61K 39/39* (2013.01); *A23V 2002/00* (2013.01); *A61K 2039/5252* (2013.01); *A61K 2039/55* (2013.01); *A61K 2039/57* (2013.01); *C12N 2760/16111* (2013.01); *C12N 2760/16134* (2013.01); *C12N 2760/16211* (2013.01); *C12N 2760/16234* (2013.01)

(58) Field of Classification Search
CPC ........ A23L 33/10; A23L 33/125; A23L 33/40; A61K 31/702; A61K 31/732; A61K 31/733; A61K 39/00; A61K 39/39; A61K 39/145

See application file for complete search history.

(56) References Cited

U.S. PATENT DOCUMENTS

| | | |
|---|---|---|
| 5,002,759 A | 3/1991 | Gaffar et al. |
| 6,576,251 B1 | 6/2003 | Stahl et al. |
| 8,591,919 B2 | 11/2013 | Stahl |
| 9,566,291 B2 | 2/2017 | Boehm et al. |
| 2002/0019991 A1 | 2/2002 | Prieto et al. |
| 2007/0274983 A1 | 11/2007 | Kluijtmans et al. |
| 2007/0275881 A1 | 11/2007 | Morrow et al. |
| 2008/0124323 A1 | 5/2008 | Boehm et al. |
| 2008/0145838 A1 | 6/2008 | Suda et al. |
| 2012/0177691 A1 | 7/2012 | Stahl et al. |

FOREIGN PATENT DOCUMENTS

| | | |
|---|---|---|
| EP | 1 597 978 A1 | 11/2005 |
| EP | 1 629 850 A1 | 3/2006 |
| EP | 1 629 850 B2 | 3/2006 |
| EP | 2 072 052 A1 | 6/2009 |
| WO | WO-99/11773 A1 | 3/1999 |
| WO | WO-99/56754 A1 | 11/1999 |
| WO | WO-00/08948 A2 | 2/2000 |
| WO | WO-01/64225 A1 | 9/2001 |
| WO | WO-2005/039319 A2 | 5/2005 |
| WO | WO-2005/039597 A2 | 5/2005 |
| WO | WO-2005/055944 A2 | 6/2005 |
| WO | WO-2007/010084 A2 | 1/2007 |
| WO | WO-2007/067053 A1 | 6/2007 |
| WO | WO-2007/105945 A2 | 9/2007 |
| WO | WO-2007/114683 A1 | 10/2007 |
| WO | WO-2009/065905 A2 | 5/2009 |
| WO | WO-2009/077352 A1 | 6/2009 |
| WO | WO-2011/008086 A1 | 1/2011 |
| WO | WO-2011/008087 A1 | 1/2011 |

OTHER PUBLICATIONS

Krathwohl, M. et al "Chemokine CXCL10 (IP-10) is sufficient to trigger an immune response . . . " Vaccine, vol. 24, pp. 2987-2993. (Year: 2006).*
Benyacoub et al., "Feeding a diet containing a fructooligosaccharide mix can enhance salmonella vaccine efficacy in mice", Journal of Immunology, 2008, pp. 123-129.
"Bioprocesses and Biotechnology for Functional Foods and Nutraceuticals", Ed. Neeser & German, 2005, pp. 104-105.
"Prebiotics in infant nutrition" S. Donovan, G. Gibson, D. Newburg,— Mead Johnson Nutr. 2008, pp. 1-37.
Annex E filed with letter of patentee on Dec. 3, 2008 in appeal proceedings relating to the opposition of the grant of EP1105002 (E17b).
Bode, "Recent advances on structure, metabolism, and function of human mil k oligosaccharides", The journal of nutrition recent advances in nutritional Sciences, 2006, vol. 136, pp. 2127-2130.
Carver J D. "Advances in nutritional modifications of infant formulas", Am J Clin Nutr, 2003, vol. 77(suppl) 1550S-1554S.
Charlwood, et al. "A detailed analysis of Neutral and Acidic Carbohydrates in Human Milk", Analytical Biochemistry, 1999, vol. 273, pp. 261-277.

(Continued)

*Primary Examiner* — Leigh C Maier

(74) *Attorney, Agent, or Firm* — Gilberto M. Villacorta; Sunit Talapatra; Foley & Lardner LLP

(57) ABSTRACT

Nutritional compositions with fucosyllactose and betagalactooligosaccharides for use in stimulation of the immune system. The composition is suitable for infants.

15 Claims, No Drawings

(56) References Cited

OTHER PUBLICATIONS

Childhood Vaccine Schedule (internet download, published in spring 2008), NIH Medline Plus, online date Apr. 10, 2013, 2 pgs.

Crittenden et al., "Production, properties and applications of food-grade oligosaccharides", Trends in Food Science& Technology, 1996, vol. 71, pp. 353-361.

Environ "GRAS Exemption claim for galacto-oligosaccharides (GOS)"application Vivinal (R), 2007, pp. 1-4.

Environ, "Generally Recognized as Safe (GRAS) Determination for the Use of Galacto-Oligosaccharides (GOS) in Foods and Term Infant Formulas", Vivinal (R), pp. 1-4, Sep. 6, 2007.

Fanaro, et al. "Galacto-oligosaccharides and long-chain fructo-oligosacchardies as prebiotics in infant formulas: A review", ACTA Pediatrica, 2005, vol. 94, Suppl 449, pp. 22-26.

Grollman, et al. "Biosynthesis of Fueosyllactose and Other Oligosaccharides Found in Milk", The Journal of Biological Chemistry, vol. 240, No. 3, Mar. 1965.

Hawley, The Condensed Chemical Dictionary, 10th ed. 1981.

Hesseling, et al. "Consensus statement on the revised World Health Organization recommendations for BCG vaccination in HIV-infected infants", Int J Tuberc Lung Disc (2008), vol. 12, No. 12, pp. 1376-1379.

Interlocutory decision in oppositions proceedings (Art. 101(3)(a) and 106(2) EPC) issued in European Application No. 04 077 394.7 dated Jul. 20, 2012.

International Search Report for PCT/NL2010/050446, dated Oct. 19, 2010, 5 pages.

Kidd, "Th1/Th2 Balance: The Hypothesis, its limitations, and implications for health and diseas", Alt Med Review, 2003, vol. 8, No. 3, pp. 223-246.

Kohlhuber, et al. "Breastfeeding rates and duration in Germany: a Bavarian cohort study", British Journal of Nutrition (May 2008), vol. 99, No. 5, pp. 1127-1132 [Epub Feb. 25, 2008].

Kovarik et al., "Optimization of vaccine responses in early life: The role of delivery systems and immunomodulators", Immunol Cell Biol, 1998, vol. 76, pp. 222-236.

Letter patentee dated Sep. 10, 2012, in reply to communication under Rule 161(1) EPC in European Application No. 10734842.7.

Milk Facts—Nutritional Components in Milk. [online]Retrieved Oct. 23, 2012 from the internet.

Mitoulas, et al. "Variation in fat, lactose and protein in human milk over 24 h and througout the first year of lactation", British Journal of Nutrition, 2002, vol. 88, pp. 29-37.

Morrow et al., "Human-milk glycans that inhibit pathogen binding protect breast-feeding infants against infectious diarrhea", The Journal of Nutrition, 2005, vol. 135, No. 5, pp. 1304-1307.

Nakamura et al, "The milk oligosaccharides of domestic farm animals", Trends in glycoscience and glycotechnology, 2004, vol. 16, No. 88, pp. 135-142.

Newburg et al., "Innate protection conferred by fucosylated oligosaccharides of human milk against diarrhea in breastfed infants", Glycobiol, 2004, vol. 14, No, 3, pp. 25-263.

Newburg et al., "Neonatal protection by an innate immune systems of human milk consisting of oligosaccharides and glycans", J Anim Sci, 2009, vol. 87, pp. 26-34.

Ninonuevo et al., "Infant formula oligosaccharides opening the gates (for speculation)", Pediatric research, 2008, vol. 64, No. 1, pp. 8-10.

Nittynen et al., "Galacto-oligosaccharides and bowel function", Scan. J. Food Nutr., 2007, vol. 51, No. 2, pp. 62-66.

Oftedal, O. T. "Lactation in the Dog: Milk Composition and Intake by Puppies", The Journal of Nutrition, vol. 114, 803-812, 1984.

Ruiz-Palacios,et al. "Campylobacter jejuni Binds Intestinal H(O) Antigen (Fucα1, 2GalB1,4GlcNAc), and Fucosyloligosaccharides of Human Milk Inhibit Its Binding and Infection", The Journal of Biological Chemistry, Issue of Apr. 18, 2003, vol. 278, No. 16, pp. 14112-14120.

Sotgiu et al., "Immunomodulation of fucosyl-lactose and lacto-N-fucopentaose on mononuclear cells from multiple sclerosis and healthy subjects", International Journal of Biomedical Science, 2006, vol. 2, No. 2, pp. 114-120.

Sumiyoshi W et al., Determination of each neutral oligosaccharide in the milk of Japanese women during the course of lactation. Br J Nutr. Jan. 2003; 89(1); 61-9.

Torres et al., "Galacto-oligosaccharides: production, properties, applications, and significance as prebiotics", Comprehensive Reviews in Food Science and Food Safety, 2010, vol. 9, pp. 438-454.

Urashima et al., "Chemical characterization of oligosaccharides in chimpanzee, bonobo, gorilla, orangutan, and siamang milk or colostrum", Glycobiology, vol. 19, No. 5, 2009, pp. 499-508.

Urashima T. et al., "Oligosaccharides of milk and colostrum in non-human mammals", Glycoconjugate Journal, 2001, vol. 18, pp. 357-371.

Vandenplas, "Oligosaccharides in Infant Formula," British Journal of Nutrition (2002) vol. 87, Suppl. 2, pp. S293-S296.

Vos et al., "A specific prebiotic oligosaccharide mixture stimulates delayed-type hypersensitivity in a murine influenza vaccination model", Int. Immunopharmacol., 2006, vol. 6, pp. 1277-1286.

Vos et al., "Dietary supplementation of neutral and acidic oligosaccharides enhances Th1-dependent vaccination responses in mice", Pediatr. Allergy Immunol., 2007, vol. 18, pp. 304-312.

Zoppi G et al., Diet and antibody response to vaccinations in healthy infants. Lancet. Jul. 2, 1983;2(8340); 11-4.

Claud et al., "Hypothesis: inappropriate colonization of the premature intestine can cause neonatal necrotizing enterocolitis", The FASEB Journal, 2001, vol. 15, No. 8, pp. 1398-1403.

Faldella et al., "The preterm infant's antibody response to a combined diphtheria, tetanus, acellular pertussis and hepatitis B vaccine", Vaccine, 1998, vol. 16, No. 17, pp. 1646-1649.

Minna-Maija et al., "Fecal microflora in healthy infants born by different methods of delivery: Permanent changes in intestinal flora after Cesarean delivery", Journal of Pediatric Gastroenterology & Nutrition, Jan. 1999, vol. 28, No. 1, pp. 19-25.

\* cited by examiner

MIXTURE OF NON-DIGESTIBLE OLIGOSACCHARIDES FOR STIMULATING THE IMMUNE SYSTEM

CROSS-REFERENCE TO RELATED APPLICATIONS

This application is a Continuation Application of U.S. patent application Ser. No. 13/383,823, filed Mar. 22, 2012, which is the National Phase of International Patent Application No. PCT/NL2010/050446, filed Jul. 12, 2010, published on Jan. 20, 2011 as WO 2011/008086 A1, which claims priority to U.S. Provisional Application No. 61/255,950, filed Oct. 29, 2009 and European Patent Application No. 09165543.1, filed Jul. 15, 2009. The contents of these applications are herein incorporated by reference in their entirety.

FIELD OF THE INVENTION

The present invention relates to nutrition with a mixture of non-digestible oligosaccharides, and in particular to the use thereof for stimulating the immune system.

BACKGROUND OF THE INVENTION

Human milk fed infants have a lower incidence of infections, including viral infections, than formula fed infants. Many components in human milk, including immunoglobulins (such as IgA), interleukin (IL)-1, IL-6, IL-8, IL-10, interferon-$\gamma$ (IFN-$\gamma$), immunocompetent cells, transforming growth factor-$\beta$ (TGF-$\beta$), lactoferrin, nucleotides, and non-digestible oligosaccharides (NDO) are thought to be involved in protection against infection with enteric or respiratory pathogens.

NDO are a major constituent of human milk and are a major element of the innate immune system of human milk. Human NDO promote the growth of a beneficial microbiota dominated by bifidobacteria and lactobacilli. Some human NDO are also known to be able to prevent directly the adhesion of pathogens and toxins.

Human milk is the preferred food for infants. However, it is not always possible or desirable to breast feed an infant. In such cases infant formulae or follow on formulae are a good alternative. These formulae should have an optimal composition in order to mimic the beneficial effects of breast milk as close as possible.

WO 2007/067053 discloses infant formula comprising the plant-derived prebiotics inulin and galacturonic acid oligosaccharide and the from lactose synthesized prebiotic transgalacto-oligosaccharide to reduce infections.

WO 2005/039597 relates to the use of acid oligosaccharide and neutral oligosaccharide for enhancing the immune system and the treatment and/or prevention of immune system related disorders.

WO 01/642255 relates to a nutritional composition comprising a prebiotic for enhancement of an immune response.

U.S. Pat. No. 6,576,251 discloses a carbohydrate mixture for dietetic foods administered by the enteral or parenteral route consisting of (a) monosaccharide(s), (b) oligosaccharide(s) (at most hexasaccharides) and (c) polysaccharide(s) (at least heptasaccharides), where the mixing ratio a, b, c, in respect of weight, is: alpha=1, b=40 to 1000, and c=1 to 50, and containing at least 1 weight percent of fucose occurring either freely and/or bound to an oligosaccharide and/or a polysaccharide. The carbohydrate mixture is said to have both a nutritional and a biological effect which is considerably greater than the corresponding action of the individual constituents.

WO 99/11773 relates to methods of producing non-human transgenic mammals which produce various oligosaccharides and glycoconjugates in their milk. Subject matter that is claimed in this document relates to the mammals themselves, the milk which they produce, compositions comprising the milk, fractions of the milk, and the purified oligosaccharides, as well as glycoconjugates, present in the milk.

WO 2005/055944 discloses a pharmaceutical composition comprising a molecule comprising a fucose group in an $\alpha$-1, 2 linkage, an $\alpha$-1, 3 linkage or an $\alpha$-1, 4 linkage to a galactose group and a pharmaceutically acceptable carrier.

WO 2007/105945 relates to a food or supplement for pregnant women comprising water soluble, non-digestible saccharides. The composition is used to improve the flora and/or immune system of the pregnant women, to improve the immune system of the infant and to improve the intestinal flora of the infant after birth.

EP 1 629 850 provides a method and composition for the treatment and/or prevention of respiratory tract infection and/or respiratory tract infection disease, said method comprising orally administering a composition to a mammal, said composition comprising a galactose containing indigestible oligosaccharide and at least 5 wt. % digestible galactose saccharide.

Much effort is dedicated to find further solutions for balancing and stimulating the immune system.

SUMMARY OF THE INVENTION

Human milk differs from milk from domestic animals in that it comprises more NDO and that the NDO are structurally different. Human NDO is very complex, since it represents a heterogenic group of more than 130 different compounds with diverse sugar composition. Because of their complex and polymorphic structure, large-scale synthesis is complicated. It is therefore not yet technically and economically feasible to prepare infant nutrition with an NDO composition identical to human milk.

Recently, new techniques have become available to chemically synthesise specific types of NDO identical to specific human NDO, thereby offering the opportunity to test the immunomodulatory capacity of specific human NDO in in vitro and in vivo assays.

The inventors unexpectedly have found that fucosyllactose (FL), an oligosaccharide present in human breast milk and with a relatively simple structure, when combined with betagalacto-oligosaccharides and preferably also with fructo-oligosaccharides and/or uronic acid oligosaccharides, showed a synergistic effect on stimulating the immune system. An increased response in delayed type hypersensitivity reaction, indicative for an increased Th1 response, was observed after vaccination with an influenza vaccine in animals having consumed the present combination of FL and betagalacto-oligosaccharides, compared to animals having consumed the single components.

It was found that the present combination, i.e. the combination comprising fucosyllactose and betagalacto-oligosaccharides and preferably further comprising fructo-oligosaccharides and/or uronic acid oligosaccharides increased the Th1 response. The effect observed was unexpectedly higher than the sum of the effects of the single components The present combination is especially advantageous for human subjects having a reduced Th1 response in comparison with healthy adults, in particular newborn infants, elderly humans suffering from immunosenescence, humans suffering from AIDS or being infected with the Human Immunodeficiency Virus, and cancer patients that are or have been subjected to chemotherapy, radiation and cancer patients that are cachectic.

The present combination is suitable for treatment and/or prevention of infections, and/or for supporting vaccination response before, during and/or after vaccination.

The present combination is especially suitable for the treatment and/or prevention of diseases which can be prevented and/or treated by an increase in Th1 response and/or Th1/Th2 balance, in particular allergy, atopic dermatitis, asthma, food allergy, allergic rhinitis (e. g. pollen allergy), dust mite allergy and other forms of hypersensitivity like systemic anaphylaxis and acute urticaria.

DETAILED DESCRIPTION

The present invention thus concerns a nutritional composition, not being human milk, comprising fucosyllactose and betagalacto-oligosaccharides.

In the context of this invention the combination comprising fucosyllactose and betagalacto-oligosaccharides and preferably further comprising fructo-oligosaccharides and/or uronic acid oligosaccharides is also referred to as the present combination. In the context of this invention, the terms a composition accordin to the invention or the composition or thepresen tcomposition means a composition comprising the present combination.

Fucosyllactose

The present combination comprises fucosyllactose. Fucosyllactose (FL) is a non-digestible oligosaccharide present in human milk. It is not present in bovine milk. It consists of three monose units, fucose, galactose and glucose linked together. Lactose is a galactose unit linked to a glucose unit via a beta 1,4 linkage. A fucose unit is linked to a galactose unit of a lactose molecule via an alpha 1,2 linkage (2'-fucosyllactose, 2'-FL) or via an alpha 1,3 linkage to the glucose unit of a lactose (3-Fucosyllactose, 3-FL). The present composition preferably comprises 2'-FL.

2'-FL, preferably α-L-Fuc-(1→2)-β-D-Gal-(1→4)-D-Glc, and 3-FL, preferably α-L-Fuc-(1→3)-[β-D-Gal-(1→4)]-D-Glc), are commercially available for instance from Sigma-Aldrich. Alternatively, they can be isolated from human milk, for example as described in Andersson & Donald, 1981, J Chromatogr. 211:170-1744, or produced by genetically modified micro-organisms, for example as described in Albermann et al, 2001, Carbohydrate Res. 334:97-103.

Preferably, a composition according to the invention comprises 1 mg to 3 g fucosyllactose per 100 ml, more preferably 10 mg to 2 g, even more preferably 20 mg to 100 mg FL per 100 ml. Based on dry weight, the present composition preferably comprises 0.007 wt % to 20 wt % fucosyllactose, more preferably 0.07 wt % to 10 wt %, even more preferably 0.15 wt % to 1 wt %. A lower amount of fucosyllactose will be less effective in stimulating the immune system, whereas a too high amount will result in unnecessary high costs of the product.

Betagalacto-oligosaccharides,

The present combination comprises betagalacto-oligosaccharides. It was found that the presence of betagalacto-oligosaccharides other than FL together with FL have a synergistic effect on immune stimulation, in particular vaccination response.

Betagalacto-oligosaccharide can also be referred to as transgalacto-oligosaccharide. In a particularly preferred embodiment the present composition comprises betagalacto-oligosaccharides ([galactose]n-glucose; wherein n is an integer from 2 to 60, i.e. 2, 3, 4, 5, 6, . . . , 59 ,60; preferably n is selected from 2, 3, 4, 5, 6, 7, 8, 9, or 10), wherein the galactose units are in majority linked together via a beta linkage. Betagalacto-oligosaccharides (TOS) are for example sold under the trademark Vivinal™ (Borculo Domo Ingredients, Netherlands). Another suitable source is Bi2Munno (Classado). Preferably the betagalacto-ologosaccharides comprises beta 1,4 and beta 1,6 linkages. Preferably the betagalacto-oligosaccharides have over 80% beta 1,4 and beta 1,6 linkages, more preferably over 90% based on total linkages linking the monomeric carbohydrate units.

Preferably the present composition comprises additional non-digestible oligosaccharides with a DP between 2 and 250, more preferably 2 to 60. The non-digestible oligosaccharide is preferably at least one, more preferably at least two, selected from the group consisting of fructo-oligosaccharides and uronic acid oligosaccharides.

The group of fructo-oligosaccharides includes inulins. Fructo-oligosaccharide is a NDO comprising a chain of beta-linked fructose units with a DP or average DP of 2 to 250, more preferably 2 to 100, even more preferably 10 to 60. Fructo-oligosaccharide includes inulin, levan and/or a mixed type of polyfructan. An especially preferred fructo-oligosaccharide is inulin. Fructo-oligosaccharide suitable for use in the compositions is also commercially available, e.g. Raftiline®HP (Orafti). Preferably the fructo-oligosaccharide has an average DP above 20.

The group of uronic acid oligosaccharides includes mannuronic acid, guluronic acid, galacturonic acid oligosaccharides, alginate dectradation products and pectin degradation products. Uronic acid oligosaccharides are preferably obtained from pectin degradation products. Hence the present composition preferably comprises a pectin degradation product with a DP between 2 and 100. Preferably the pectin degradation product is prepared from apple pectin, beet pectin and/or citrus pectin. Preferably the uronic acid oligosaccharide is a galacturonic acid oligosaccharide.

In a preferred embodiment the composition comprises a mixture of betagalacto-oligosaccharides and fructo-oligosaccharides selected from the group consisting of short chain fructo-oligosaccharides and inulin, more preferably inulin. A mixture of at least two different non-digestible oligosaccharides advantageously stimulates the beneficial bacteria of the intestinal microbiota to a greater extent. Preferably the weight ratio in a mixture of betagalacto-oligosaccharides and fructo-oligosaccharide, is between 25 and 0.05, more preferably between 20 and 1. Preferably the present composition comprises betagalacto-oligosaccharides with a degree of polymerization (DP) of 2 to 10 and/or fructo-oligosaccharides with a DP of 2 to 60.

Besides FL, most preferably the composition comprises betagalacto-oligosaccharide, fructo-oligosaccharide and a uronic acid oligosaccharide. It was found that such a combination acts synergistically with fucosyllactose, in particular 2'-fucosyllactose. The weight ratio betagalacto-oligosaccharide:fructo-oligosaccharide:uronic acid oligosaccharide is preferably (20 to 2):1:(1 to 20), more preferably (20 to 2):1:(1 to 10), even more preferably (20 to 2):1:(1 to 3), even more preferably (12 to 7):1:(1 to 2). Most preferably the weight ratio is about 9:1:1.1. Preferably the weight ratio FL to betagalacto-oligosaccharide, preferably TOS, is from 5 to 0.05, more preferably 5 to 0.1, more preferably from 2 to 0.1. Preferably the weight ratio FL to fructo-oligosaccharide, preferably inulin, is from 10 to 0.05, more preferably 10 to 0.1, more preferably from 2 to 0.5. Preferably the weight ratio FL to uronic acid oligosaccharide, preferably derived from pectin, is from 10 to 0.05, more preferably 10 to 0.1 more preferably from 2 to 0.5.

Preferably, the composition comprises 80 mg to 4 g non-digestible oligosaccharides, including fucosyllactose and betagalacto-oligosaccharides, per 100 ml, more preferably 150 mg to 2 g, even more preferably 300 mg to 1 g non-digestible oligosaccharides per 100 ml. Based on dry weight, the composition preferably comprises 0.25 wt % to 25 wt % non-digestible oligosaccharides, more preferably 0.5 wt % to 10 wt %, even more preferably 1.5 wt % to 7.5 wt %. A lower amount of non-digestible oligosaccharides will be less effective in stimulating the beneficial bacteria in the microbiota, whereas a too high amount will result in side-effects of bloating and abdominal discomfort.

Nutritional Composition

The present combination of FL and betagalato-oligosaccharides is preferably a nutritional composition. The composition of the present invention is not human milk. The present composition is preferably enterally administered, more preferably orally.

The present composition is preferably a nutritional formula, preferably an infant formula. The present composition can be advantageously applied as a complete nutrition for infants. The present composition preferably comprises a lipid component, protein component and carbohydrate component and is preferably administered in liquid form. The present invention includes dry food, preferably a. powders which is accompanied with instructions as to admix said dry food mixture with a suitable liquid, preferably with water.

The present invention advantageously provides a composition wherein the lipid component provides 5 to 50% of the total calories, the protein component provides 5 to 50% of the total calories, and the digestible carbohydrate component provides 15 to 85% of the total calories. The present invention advantageously provides a composition wherein the lipid component provides 20 to 50% of the total calories, the protein component provides 5 to 30% of the total calories, and the digestible carbohydrate component provides 30 to 70% of the total calories. Preferably, in the present composition the lipid component provides 35 to 50% of the total calories, the protein component provides 7.5 to 12.5% of the total calories, and the digestible carbohydrate component provides 40 to 55% of the total calories. For calculation of the % of total calories for the protein component, the total of energy provided by the proteins, peptides and amino acids needs to be taken into account.

The present composition preferably comprises at least one lipid selected from the group consisting of animal lipid, excluding human lipids, and vegetable lipids. Preferably the present composition comprises a combination of vegetable lipids and at least one oil selected from the group consisting of fish oil, animal oil, algae oil, fungal oil, and bacterial oil. The present composition preferably comprises long chain poly-unsaturated fatty acids (LC-PUFA). LC-PUFA are fatty acids or fatty acyl chains with a length of 20 to 24 carbon atoms, preferably 20 or 22 carbon atoms comprising two or more unsaturated bonds. More preferably the present composition comprises eicosapentaenoic acid (EPA, n-3), docosahexaenoic acid (DHA, n-3) and/or arachidonic acid (ARA, n-6).

Preferably the present composition comprises at least 0.1 wt. %, preferably at least 0.25 wt. %, more preferably at least 0.6 wt. %, even more preferably at least 0.75 wt. % LC-PUFA with 20 and 22 carbon atoms based on total fat content.

The content of LC-PUFA, particularly the LC-PUFA with 20 and 22 carbon atoms, preferably does not exceed 6 wt %, more preferably does not exceed 3 wt. % of the total fat content as it is desirable to mimic human milk as closely as possible. The LC-PUFA may be provided as free fatty acids, in triglyceride form, in diglyceride form, in monoglyceride form, in phospholipid form, or as a mixture of one of more of the above. The present composition preferably comprises between 5 and 75 wt. % polyunsaturated fatty acids based on total fat, preferably between 10 and 50 wt. %.

The protein used in the nutritional composition is preferably selected from the group consisting of non-human animal proteins (preferably milk proteins), vegetable proteins (preferably soy protein and/or rice protein), hydrolysates thereof, free amino acids and mixtures thereof. The present composition preferably contains casein, whey, hydrolyzed casein and/or hydrolyzed whey protein. Preferably the protein comprises intact proteins, more preferably intact bovine whey proteins and/or intact bovine casein proteins.

The present composition preferably contains digestible carbohydrates selected from the group consisting of sucrose, lactose, glucose, fructose, corn syrup solids, starch and maltodextrins, more preferably lactose.

In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

Preferably the present composition comprises nucleotides and/or nucleosides, more preferably nucleotides. Preferably, the composition comprises cytidine 5'-monophospate, uridine 5'-monophospate, adenosine 5'-monophospate, guanosine 5'-monophospate, and/or inosine 5'-monophospate, more preferably cytidine 5'-monophospate, uridine 5'-monophospate, adenosine 5'-monophospate, guanosine 5'-monophospate, and inosine 5'-monophospate. Preferably the composition comprises 5 to 100, more preferably 5 to 50 mg, most preferably 10 to 50 mg nucleotides and/or nucleosides per 100 gram dry weight of the composition. The presence of nucleotides and/or nucleotides advantageously stimulate NK cell activity. The nucleotides and/or nucleosides are deemed to act synergistically with the fucosyllactose of the present composition.

Application

The present combination of FL and betagalato-oligosaccharides was found to synergistically stimulate the immune-system. In particularly the Th1 response was increased. The effect of the combination of these two components is higher than the sum of the effects of the single components.

The present combination can advantageously be used in the treatment and/or prevention of a disease, and thus the invention concerns a method for the treatment and/or prevention of a disease in a mammal, said method comprising administering the present combination to the mammal. In other words, the invention also concerns the use of a combination according to the present invention for the manufacture of a composition, preferably a nutritional composition, for the treatment and/or prevention of a disease. In other words the invention concerns a composition or nutritional composition comprising a combination according to the present invention for use in the treatment and/or prevention of a disease. Preferably the mammal is a human, even more preferably a human infant. Thus the invention also concerns the use of a combination according to the present invention for the manufacture of a composition, preferably a nutritional preparation, for the treatment and/or prevention of a disease in an infant. Or in other words the invention concerns a composition or nutritional composition comprising a combination according to the present invention for use in the treatment and/or prevention of a disease in an infant.

In the context of this invention, an infant is in the age of 0 to 6 years, preferably in the age of 0 to 4 years, preferably in the age of 0 to 2 years, preferably in the age of 0 to 1 year.

Also the invention concerns a method for providing nutrition to an infant, said method comprising administering the present combination or nutitional composition to the infant. In other words, the invention also concerns the use of a combination according to the present invention for the manufacture of a nutritional composition for providing nutrition to an infant. In other words the invention concerns a composition or nutritional composition comprisng a combination according to the present invention for use in providing nutrition to an infant.

The present combination can advantageously be used to increase the Th1 response, increase the Th1/Th2 balance, restore imbalance in the Th1/Th2 responses, maintain a favorable Th1/Th2 balance and/or for the treatment and prevention of disorders which are associated with a Th1/Th2 imbalance. Hence, compositions which are advertised to e.g. simulate maturation of the immune system, enhance the resistance to pathogens by enhancing the immune system and/or support the immune system are part of the present invention. In a further aspect, the present invention provides a method for the treatment and/or prevention of an immune system related disorder, said method comprising administering to said mammal a composition comprising a therapeutically effective amount of the present combination. In a further aspect, the present invention provides a method of enhancing the immune response in a mammal said method comprising administering to the mammal the present combination.

The immune system of newborn human infants is characterized by an excess of Th2 response. During maturation of the immune system, the Th1 response increases and the Th1/Th2 balance shifts to values observed for healthy adults. Hence, the present combination is especially advantageous for human infants. The present invention supports the maturation of the immune system in infants. In a further embodiment, the method of the invention relates to the administration of the present combination to humans in the age of 0 to 6 years, preferably in the age of 0 to 4 years, preferably in the age of 0 to 2 years, more preferably in the age of 0 to 1 year. In a preferred embodiment the present method relates to the stimulation of the maturation of the immune system in human subjects in the age of 0-6 years, preferably in the age of 0 to 4 years, preferably in the age of 0 to 2 years, more preferably in the age of 0 to 1 year.

The composition comprising fucosyllactose and betagalacto-oligosaccharides even more advantageously is used in preterm infants and/or very low or low birth weight infants, since these infants are even more vulnerable and/or prone to viral infections.

The composition comprising fucosyllactose and betagalacto-oligosaccharide even more advantageously is used in infants delivered via Caesarean section. Caesarean section born infants are born in a hospital in an environment having more pathogens against which the antibodies, conferred by the mother to the infant, are not effective. Caesarean section born infants have a delayed and less optimal colonization of the large intestinal tract and therefore are also more prone to intestinal infections A too low Th1/Th2 balance leads to extreme sensitivity towards foreign components which could lead to a variety of immunological reactions, e.g. allergies and related diseases such as atopic dermatitis, asthma, food allergy, allergic rhinitis (e. g. pollen allergy), dust mite allergy and other forms of hypersensitivity like systemic anaphylaxis and acute urticaria. Hence, the present combination is especially advantageous for treatment and/or prevention of a disorder selected from the group consisting of allergy, food allergy, atopic dermatitis, asthma, allergic rhinitis, dust mite allergy and urticaria. The present invention increases the Th1/Th2 balance.

An increase in Th1 response leads to an increase in the response against pathogenic bacteria and/or viruses. Hence, the present combination is suitable for the treatment and/or prevention of infections. The present preparation can be advantageously used for the treatment and/or prevention of intestinal infections, systemic infections and/or respiratory tract infections.

Since the combination of FL and betagalacto-oligosaccharides was found to specificially synergistically enhance the Th1 response, the present invention is particularly suitable to prevent viral infections, more preferably viral infections caused by orthomyxoviridae, in particular the influenza virus, herpesviridae, rotavirus, cytomegalovirus, caliciviridae, respiratory syncytial virus, human imunofeficiency virus and/or rhinovirus. The use of the present invention is therefore preferably for preventing and/or treating viral infections, more preferably the viral infections common cold, flu, measles, chicken pox, viral diarrhoea, viral gastroenteritis, HIV infection and/or viral respiratory tract infections.

It was also found that the present combination can suitably be used to support vaccination processes, e.g. enhance the effects of a vaccination process. The present combination is suitable for supporting vaccination response before, during and/or after vaccination. Particularly the effects of vaccinations for diptheria-tetanus, pertussis, polio vaccine, measles/mumps/rubella, pneumococcal conjugate, haemophilus B conjugate, hepatitis B, hepatitis A, varicella, andor influenza can suitably be enhanced. Hence, the present combination is advantageously used in the treatment and/or prevention of infections, and/or for use in enhancement of vaccination response.

Hence, the present combination is advantageous for human subjects suffering from immune deficiencies, in particular elderly humans suffering from immunosenescence, humans suffering from AIDS or being infected with the Human Immunodeficiency Virus, and/or cancer patients, more particular cancer patients that are or have been subjected to chemotherapy, radiation and cancer patients that are cachectic.

The present composition is advantageously used for nutriton for elderly. Elderly have a decreased Th1 response. Elderly are especially vulnerable to viral infection complications. In a preferred embodiment the present invention is used for treatment and/or prevention of immunosenescence in elderly. In one embodiment, the present invention concerns providing nutrition to an elderly person. An elderly person is a person having an age of 55 years or more, in particular of the age of 65 or more.

EXAMPLES

Example 1

The effect of diets comprising 2'-FL and/or betagalacto-oligosaccharides was tested in a mouse model wherein a response to an antigen is measured by a delayed-type hypersensitivity (DTH) response. This DTH response in the ears after local challenge with an antigen present in a vaccine is a measure of Th1 cell proliferation. During response to infection and/or vaccination Th1 cells proliferate in response to the challenge with the antigen. These Th1 cells infiltrate the ear when the ear is subsequently challenged with the antigen and cause swelling. Infiltration with the Th1 cells in the ear takes about 24 h and the swelling is therefore delayed. The more Th1 cells proliferated during initial vaccination and/or infection, the more DTH upon challenging with the antigen is observed.

Materials and Methods 6-8 Weeks old female C57BL/6 mice (Charles River) received semi-purified AIN-93G-based diets (Research Diet Service, Wijk bij Duurstede, the Netherlands), comprising 1) 1 wt % betagalacto-oligosaccharide (GOS, source Vivinal GOS, Borculo Domo), fructo-oligosaccharide (FOS, Source RaftilineHP, Orafti) and galacturonic acid oligosaccharide (source AOS) in a 9:1:1.1 ratio. AOS were produced from pectin (Südzucker A G, Mannheim, Germany), with a DP of 1-20. It consists of approximately 75% galacturonic acid oligomers, based on total weight, 2) 1 wt % 2'fucosyllactose (2'-FL), 3) 1 wt % betagalacto-oligosaccharides, fructo-oligosaccharides and galacturonic acid oligosaccharide (AOS) in a 9:1:1.1 ratio and 1 wt % 2'-FL.

4) 0.5 wt % betagalacto-oligosaccharides, fructo-oligosaccharides and galacturonic acid oligosaccharide (AOS) in a 9:1:1.1 ratio and 0.5 wt % 2'-FL.

All groups were compared to the unsupplemented control diet (control and sham control group). Dietary supplementation started 14 days before the first vaccination and lasted until the end of the experiment, 31 days after the first vaccination.

Vaccination experiments were performed using Influvac (Solvay Pharmaceuticals, Weesp, the Netherlands) from season 2005/2006. The mice received a primary vaccination and a booster vaccination, consisting of a subcutaneous (sc) injection of a 1:1 mix of vaccine and adjuvant in a total volume of 100 µl. The booster vaccination was given at 21 days after the primary vaccination. The experiments ended 10 days after booster vaccination. Negative control groups that were included received injections with a 1:1 mix of PBS and adjuvant in a total volume of 100 µl (sham control). Ear thickness was measured in duplicate before vaccine challenge and 24 h thereafter, using a digital micrometer (Mitutoyo Digimatic 293561, Veenendaal, the Netherlands). The DTH response was calculated by subtracting the basal ear thickness from the value at 24 h after challenge.

Results

Supplementation with GOS/FOS/AOS, or 2' FL alone resulted in an increased ear swelling. However, the combination of 2'FL and GOS/FOS/AOS resulted in an even higher increase of the DTH response, a TH1-dependent parameter, compared with control-fed animals and compared with the single components. The combination synergistically increased vaccination response. See Table 1.

TABLE 1

Effect of 2'-FL and TOS on DTH response.

| Dietary intervention | Earswelling DTH (se) | Δ DTH µm | Relative DTH |
|---|---|---|---|
| Sham control | 19.3 (5.5) | 0 | 0 |
| Control | 66.3 (6.4) | 47.0 | 1 |
| 1% TOS/FOS/AOS | 90.8 (7.5) | 71.5 | 1.52 |
| 1% 2'-FL | 99.7* (10.2) | 80.4 | 1.71 |
| 0.5% TOS/FOS/AOS, 0.5% 2'-FL | 117.8** (4.4) | 98.5 | 2.10 |
| expected | 95.3 | 76.0 | 1.62 |

*indicates $p < 0.05$ compared to control group
**indicates $p < 0.01$ compared to control group and $p < 0.05$ compared to 0.5% GOS/FOS/AOS.

As the effect on DTH response is significantly higher (110%) than the DTH responses from diets containing the FL (71%) or betagalacto-oligosaccharides (52%) alone, and also much higher than based on the additive effect of which an be calculated to be 62% increase of DTH, these results are indicative for the synergistic effect provided by the administration of FL and betagalato-oligosaccharides, and preferably fructo-oligosaccharides and/or uronic acid oligosaccharides, on Th1 response increase.

Overall, these results support that oral supplementation with FL in combination with betagalacto-oligosaccharides, more preferably additionaly comprising fructo-oligosaccharides and/or uronic acid oligosaccharides, stimulates the immune response. The immune response is in particular enhanced with respect to the Th1 response and/or the vaccination response. The results are also indicative for an increased Th1/Th2 balance.

The results of this experiment are an indication that the present invention can advantageously be used for support in vaccination response. The results of this experiment are also an indication that it can advantageously be used in subjects with a low Th1 response, in particular infants. The results of this experiment are also an indication that it can advantageously be used in subjects with a low Th1 response, in particular elderly suffering or at risk for suffering from immunosenescence, HIV patients, AIDS patients and/or cancer patients that are or have been subjected to chemotherapy and/or radiation or that are cachectic. This model is indicative for basic immunological changes, which can be beneficial in all disorders with malfunctioning immune system.

Example 2

Infant formula for stimulating immune system comprising per 100 ml (13.9 dry weight):
  1.4 g protein (whey and casein)
  7.3 g digestible carbohydrates (including lactose)
  3.6 g fat (vegetable fat, fish oil)
  0.8 g non-digestible oligosaccharides of which 80 mg 2'-fucosyllactose and 640 mg beta-galacto-oligosaccharides, and 80 mg fructo-oligosaccharides Further are included: choline, myo-inositol, taurine, minerals, trace elements, and vitamins as known in the art.

Example 3

Infant formula for stimulating immune system comprising per 100 ml (13.9 dry weight):
  1.4 g protein (whey and casein)
  7.3 g digestible carbohydrates (including lactose)
  3.6 g fat (vegetable fat, fish oil)

0.8 g non-digestible oligosaccharides of which 40 mg 2'-fucosyllactose and 760 mg beta-galacto-oligosaccharides, fructo-oligosaccharides and uronic acid oligosaccharides in a 9:1:1.2 wt/wt ratio.

Further are included: choline, myo-inositol, taurine, minerals, trace elements, and vitamins as known in the art.

The invention claimed is:

1. A nutritional composition, comprising: (a) 2'-fucosyllactose and betagalacto-oligosaccharides, (b) protein, wherein protein provides 5 to 50% of total calories in the composition, (c) digestible carbohydrates, wherein digestible carbohydrates provide 15 to 85% of total calories in the composition, and (d) fat comprising vegetable lipids, wherein fat provides 5 to 50% of total calories in the composition.

2. The nutritional composition according to claim 1, further comprising fructo-oligosaccharides and/or uronic acid oligosaccharides.

3. The nutritional composition according to claim 1, further comprising fructo-oligosaccharides and uronic acid oligosaccharides.

4. The nutritional composition according to claim 1, wherein the betagalacto-oligosaccharides have over 80% beta 1,4 and beta 1,6 linkages.

5. The nutritional composition according to claim 1, having 0.07 to 1 wt. % 2'-fucosyllactose and/or 0.25 wt % to 15 wt % of the sum of betagalacto-oligosaccharides, fructo-oligosaccharides and uronic acid oligosaccharides based on dry weight of the composition.

6. A method of stimulating the immune system, comprising administering to a mammal in need thereof a composition according to claim 1.

7. The method according to claim 6, wherein the immune system is stimulated by increasing Th1 response, or increasing Th1/Th2 balance or both.

8. The method according to claim 6, wherein the mammal is an infant.

9. A method of enhancement of a vaccination response in a mammal, comprising administering to the mammal a composition according to claim 1.

10. The method according to claim 9, wherein the mammal is an infant.

11. A method of treatment and/or prevention of infections, comprising administering to a mammal in need thereof a composition according to claim 1.

12. The method according to claim 11, wherein the mammal is an infant.

13. The composition according to claim 1, which is an infant formula.

14. The method according to claim 8, wherein the infant is an infant delivered via Caesarean section.

15. The method according to claim 12, wherein the infant is an infant delivered via Caesarean section.

* * * * *